United States Patent [19]

Ibsen et al.

[11] Patent Number: 5,334,625
[45] Date of Patent: Aug. 2, 1994

[54] RESTORATIVE DENTAL ADHESIVE COMPOSITION

[75] Inventors: Robert L. Ibsen; Donald R. Pacropis, both of Santa Maria; William R. Glace, Orcutt, all of Calif.

[73] Assignee: Den-Mat Corporation, Santa Maria, Calif.

[21] Appl. No.: 774,551

[22] Filed: Oct. 10, 1991

Related U.S. Application Data

[63] Continuation-in-part of Ser. No. 561,194, Aug. 1, 1990, Pat. No. 5,151,453, which is a continuation of Ser. No. 333,904, Apr. 6, 1989, abandoned.

[51] Int. Cl.$^5$ .................................................. C08F 2/44
[52] U.S. Cl. .................................... 523/115; 523/116; 523/117; 523/118; 424/78.31; 526/326; 525/330.5
[58] Field of Search ............... 523/115, 116, 118, 117; 525/330.5; 424/78.31; 526/326

[56] References Cited

U.S. PATENT DOCUMENTS

| | | | |
|---|---|---|---|
| 4,659,75 | 4/1987 | Bowen | 523/116 |
| 4,674,980 | 6/1987 | Ibsen et al. | 523/116 |
| 4,738,722 | 4/1988 | Ibsen et al. | 523/116 |
| 4,746,686 | 5/1988 | Waller | 523/116 |

Primary Examiner—Paul R. Michl
Assistant Examiner—Raj Bawa
Attorney, Agent, or Firm—Spensley Horn Jubas & Lubitz

[57] ABSTRACT

An adhesive composition useful for restoration comprising a finely-divided reinforcing filler, a polymerizable matrix material, a bonding agent, a coupling agent, and a thermal initiator.

8 Claims, No Drawings

RESTORATIVE DENTAL ADHESIVE COMPOSITION

This application is a continuation-in-part of application Ser. No. 561,194, filed Aug. 1, 1990 now U.S. Pat. No. 5,151,453, issued Sep. 29, 1992, which is a continuation application of Ser. No. 333,904, filed Apr. 6, 1989, now abandoned.

BACKGROUND OF THE INVENTION

1. Field of the Invention

This invention relates to adhesive compositions useful for restoration, including their use as light-curable dental cements, which possess improved bonding strength and curing property.

2. Description of the Prior Art

Glass ionomer dental cements are a new class of restorative material for use in dentistry. Compositions such as these have been in clinical use since 1975 in Europe and were introduced in the United States in 1977. Glass ionomer cements are composed of silica cement and polyacrylic acid, and have characteristics pertaining to both constituents.

Although glass ionomer cements have been accepted by dental practitioners, because they are tooth colored, bond to dentin and enamel, and contain fluoride ions, these cements have significant drawbacks. For example, glass ionomers are aesthetically inferior to dental composite resins, susceptible to water contamination, and relatively slow to cure. However, progress has been made in developing improved glass ionomer cements, as is illustrated in U.S. Pat. No. 4,738,722 to Ibsen, et al. The Ibsen patent describes a buffered glass ionomer dental cement which minimizes pulpal irritation upon application and expedites curing time.

This invention provides advances in the area of dentistry by offering unique adhesive restorations which release fluoride, and dual cured, can be radiopaque yet can be visually translucent, and bond to all dental substrates with minimum substrate preparation. Since the dental cement of this invention is non-aqueous, it has the additional property of increased resistance to dissolution.

Some of the above-noted properties of the dental adhesive are appreciated not only in dental uses, but for repairing or bonding a variety of materials. Thus, this invention also provides for restorative adhesives adapted for use in non-dental fields, such as repair glue or bone cement.

SUMMARY OF THE INVENTION

Unexpectedly, it has been found that certain dental adhesive materials, which are hereto unavailable for cement application, can be effectively formulated in a light- or thermo-curable dental cement composition to produce stronger adhesion to dentin than could be previously achieved. Further surprisingly, it has been found that these same dental adhesive materials can be utilized as a restorative adhesive in wide application not related to dentistry.

In accordance with this invention, there is provided a restorative adhesive composition comprising a finely-divided reinforcing filler, a polymerizable matrix material, a thermal initiator, a coupling agent, and a bonding agent. Preferably, the composition may further include a hydrophilic resin and a photoinitiator.

In one aspect of this invention, there is provided a dental cement composition comprising:

(a) a finely-divided dental filler;
(b) a methacrylate-functional resin;
(c) a bonding agent selected from the group consisting of (i) N-phenylglycine, the alkali metal salt thereof, or the mixture of the foregoing two compounds, (ii) the adduct of N(p-tolyl)glycine and glycidyl methacrylate, the alkali metal salt thereof, or the mixture of the foregoing two compounds, and (iii) the adduct of N-phenylglycine and glycidyl methacrylate, the alkali metal salt thereof, or the mixture of the foregoing two compounds;
(d) a coupling agent selected from the group consisting of (i) the adduct of pyromellitic acid dianhydride and 2-hydroxyethyl methacrylate, (ii) the adduct of 2,2',4,4'-benophenonetetra-carboxylic dianhydride and 2-hydroxyethyl methacrylate, (iii) 4-methacryloxyethyltrimellitic anhydride; and (iv) other compounds containing at least one group or moiety capable of free radical polymerization and at least one aromatic ring or moiety containing electron-withdrawing substituents that do not interfere with free radical polymerization;
(e) a polymerizable carboxylic acid;
(f) a hydrophilic resin;
(g) a photoinitiator; and
(h) a thermal initiator.

In another aspect of this invention, there is now provided for the first time a light-curable dental cement composition comprising in a two component system:

(a) a first component comprising: (1) a finely-divided dental filler; (2) a bonding agent selected from the group consisting of (i) N-phenylglycine, the alkali metal salt thereof, or the mixture of the foregoing two compounds, (ii) the adduct of N(p-tolyl)glycine and glycidyl methacrylate, the alkali metal salt thereof, or the mixture of the foregoing two compounds, and (iii) the adduct of N-phenylglycine and glycidyl methacrylate, the alkali metal salt thereof, or the mixture of the foregoing two compounds; (3) a photoinitiator; if desired, a radiopaquing agent; and, if desired, a buffering agent; and (b) a second component comprising: (1) a methacrylate-functional resin, (2) a hydrophilic resin; (3) a coupling agent selected from the group consisting of (i) the adduct of pyromellitic acid dianhydride and 2-hydroxyethyl methacrylate, (ii) the adduct of 3,3',4,4'-benophenonetetra-carboxylic dianhydride and 2-hydroxyethylmethacrylate, (iii) 4-methacryloxyethyltrimellitic anhydride, and (iv) other compounds containing at least one group or moiety capable of free radical polymerization and at least one aromatic ring or moiety containing electron-withdrawing substituents that do not interfere with free radical polymerization; (4) a photoinitiator; (5) a polymerizable carboxylic acid; (6) a free-radical scavenger; and (7) a thermal initiator.

Alternatively, there is provided a light-curable dental cement composition comprising in a two-component system:

(a) a first component comprising: (1) a finely-divided dental filler; (2) a hydrophilic resin; (3) a methacrylate-functional resin; (4) a photoinitiator; (5) a free-radical scavenger; (6) a thermal initiator; (7) a polymerizable carboxylic acid; (8) a coupling agent selected from the group consisting of (i) the adduct of pyromellitic acid dianhydride and 2-hydroxyethyl methacrylate; (ii) the adduct of 3,3',4,4', -benzophenonetetracarboxylic dianhydride and 2-hydroxyethyl methacrylate, and (iii) 4-methacryloxyethyltrimellitic anhydride; and (iv) other compounds containing at least one group or moiety capable of free radical polymerization and at least one aromatic ring or moiety containing electron-withdrawing substituents that do not interfere with free radical polymerization.

(b) a second component comprising: (1) a finely-divided dental filler; (2) a hydrophilic resin; (3) a methacrylate-functional resin; (4) a bonding agent selected from the group consisting of (i) N-phenylglycine, the alkali metal salt thereof, or the mixture of the foregoing two compounds, (ii) the adduct of N(p-tolyl)glycine and glycidyl methacrylate, the alkali metal salt thereof, or the mixture of the foregoing two compounds, and (iii) the adduct of N-phenylglycine and glycidyl methacrylate, the alkali metal salt thereof, or the mixture of the foregoing two compounds; (5) a photoinitiator; if desired, a radiopaquing agent; and, if desired, a buffering agent.

DESCRIPTION OF THE PREFERRED EMBODIMENTS

The essential ingredients of the adhesive composition of this invention should preferably be non-toxic, biocompatible, and comprise a finely-divided reinforcing filler, a polymerizable matrix material, a thermal initiator, a coupling agent, and a bonding agent. Preferable but optional ingredients that can be included in the above composition are a hydrophilic resin, a polymerizable carboxylic acid, a free-radical scavenger, a radiopaquing agent, a buffering agent, a photoinitiator, and a pigment.

More specifically, the various ingredients of the restorative adhesive composition in accordance with this invention are explained hereinbelow by way of a dental composition:

1. Reinforcing Filler

Any inert reinforcing filler currently used or usable in the bonding or repairing technology can be employed. If the use of the adhesive is contemplated in dental applications, a preferred type of filler is that from which fluoride ions can leach. The release of fluoride ions causes a significant decrease in the enamel decay at the filler-tooth interface, thus enhancing the protective effect of the filler. Preferred fillers include, but are not limited to apatite, soda glass, barium glass, strontium glass, borosilicate glass, silica, fumed silica, flint silica, alumina, quartz, aluminum silicate, lithium aluminum silicate, and alumina fluoride silicate. For non-dental purposes, porcelain, ceramic fibers, and zirconium oxide may be used.

Particularly preferred is an alumina fluoride silicate glass made by and available from Specialty Glass Company of Oldsman, Fla., and identified as SP912-1 Glass. Another preferred material is a barium fluoride silicate glass available from Industrial Corp. of Glenmoore, Pa., and from Den-mat Corporation of Santa Maria, Calif. These particular glasses impart radiopacity, yet they are optically more translucent than other glasses. The particle size of the filler ranges from about 0.005 to about 500 microns.

2. Radiopaquing Agent

Barium salts, such as barium sulfate, barium tungstate or barium aluminum borosilicate may be used as a radiopaquing agent.

3. Buffering Agent

A buffering agent such as zinc oxide or titanium dioxide is used to adjust a final dental cement composition to a pH between 5 and 7. The buffered composition should have the pH close to neutral, thus avoiding pulpal irritation upon application.

4. Bonding Agent

Improved bonding (strong adhesion) of dental cements to dentin and enamel is conferred to the cements by the inclusion of known dental bonding agents. Suitable bonding agents include, but are not limited to, those described in U.S. Pat. No. 4,659,751 to Bowen, et al., the disclosure of which is herein incorporated by reference.

Preferably, this invention uses at least one bonding agent selected from the group consisting of (1) N-phenylglycine (NPG), the alkali metal thereof, or the mixture of the foregoing two compounds; (2) the adduct of N(P-tolyl)glycine and glycidyl methacrylate (NPG-GMA), the alkali metal salt thereof, or the mixture of the foregoing two compounds; and (3) the adduct of N-phenylglycine and glycidyl methacrylate (NPG-GMA), the alkali metal salt thereof, or the mixture of the foregoing two compounds.

The alkali-metal salts of the above-indicated amino acids provide significantly stronger bonding than NPG, NPG-GMA, or NTG-GMA, alone. U.S. Pat. No. 4,964,911 to Ibsen, et al. describes the use of these amino acids as a dentin coating layer.

5. Photoinitiator

According to one aspect this invention, the light-initiated curing of a polymerizable matrix material involves photosensitization of light-sensitive compounds by ultraviolet or visible light, which, in turn, initiates polymerization of the matrix material. The photoinitiator to be used in this invention comprises a combination of a photosensitive ketone (an acceptor in exciplexes) and a tertiary amine (a donor in exciplexes). Typical photosensitive ketones include benzophenone, acetophenone, thioxanthen-9-one, 9-fluorenone, anthraquinone, 4'-methoxyacetophenone, diethoxyacetophenone, biacetyl, 2,3-pentadione, benzyl, 4,4'-methoxybenzil, 4,4'-oxidibenzil, and 2,3-bornadione (dl camphroquinone). Typical tertiary amines include ethyl-4-dimethyl amino benzoate, ethyl-2-dimethyl amino benzoate, 4,4-bis(dimethylamino) benzophenone, n-methyldiethanolamine, and dimethylaminobenzaldehyde.

A preferred combination of the photoinitiators is 2,3-bornanedione with ethyl-4-dimethyl amino benzoate. Other suitable initiators are illustrated in U.S. Pat. No. 4,674,980 to Ibsen, et al., the disclosure of which is incorporated by reference.

Alternatively, any known photosensitizing system which can function effectively in a dental cement composition when exposed to light may substitute for the above-named compounds or combinations. The amount of the photoinitiator should be sufficient to initiate polymerization in a selected resin and complete it in depth within about half a minute when the filler-resin composition is exposed to a visible-light output of at least 5,000 foot candles.

6. Polymerizable Matrix Material

Typically, a low toxicity methacrylate-functional resin such as ethoxylated bisphenol A dimethacrylate, or Bis-GMA (the adduct of bisphenol A and glycidyl methacrylate), is used as a polymerizable matrix material. Also, a mixture of the two agents with bisphenol A dimethacrylate may be used.

7. Hydrophilic Resin

A hydrophilic co-monomer such as 2-hydroxyethyl methacrylate or hydroxypropyl methacrylate is used to make the dental composition of this invention sufficiently hydrophilic to dentine.

8. Free-Radical Scavenger

Any known free-radical scavenger (anti-oxidants) such as butylated hydroxytoluene can be used to scavenge small amounts of free radicals generated during extended shelf storage.

9. Polymerizable Carboxylic Acid

The polymerizable carboxylic acids to be used together with the dental fillers can be selected from any currently used in dental composites. Typical acids are polyacrylic acid, polymaleic acid, polyitaconic acid, or a copolymer of acrylic acid, maleic acid and itaconic acid. These polymers should have molecular weights MW of 3,000-250,000 and can be easily prepared by conventional techniques. Preferably, the polymerizable carboxylic acid is used in combination with d-tartaric acid.

10. Thermal Initiator

Benzoyl peroxide or other suitable peroxides may initiate polymerization of the polymerizable matrix material. Addition of such thermal initiators is necessary to insure complete polymerization. Even when light alone does not cure the matrix material, the peroxide initiates curing of the uncured material thermally upon standing. Benzoyl peroxide may be used together with 2-hydroxyethyl-p-toluidine.

11. Coupling Agent

A monomeric coupling agent may be included in the dental composition of this invention in order to further strengthen the bonding between the dental composition and dentin. Suitable coupling agents are selected from the group consisting of (1) the adduct of pyromellitic acid dianhydride and 2-hydroxyethyl methacrylate (PMDM); (2) the adduct of 3,3',4,4'-benzophenonetetracarboxylic dianhydride and 2-hydroxyethyl methacrylate (BTDA-HEMA); (3) 4-methacryloxyethyltrimellitic (4-META); and (4) other compounds containing at least one group or moiety capable of free radical polymerization, and at least one aromatic ring or moiety containing electron-withdrawing substituents which do not interfere with free radical polymerization. Among others, PMDM is most preferred.

12. Other Components

Pigments such as iron oxide or titanium oxide are incorporated in the dental composition to impart a more toothlike color.

Also, a color stabilizing agent such as 2,2-hydroxy-5-test-octylphenylbenztriazole may be included in the dental composition to improve its aesthetic property.

The restorative adhesive composition of this invention can assume several forms when applied to a tooth: a powder-liquid form; a paste-paste form; a paste-powder form; and a gel-powder form.

These preferred forms will be illustrated in order.

Powder-Liquid Systems

In general, the powder form comprises a dental filler, a radiopaquing agent (optional), a buffering agent (optional), a bonding agent, and a photoinitiator. The dental filler may be a mixture of some or several of the aforementioned dental fillers. The liquid form comprises a photopolymerizable matrix material, a hydrophilic resin, a coupling agent, an matrix adhesive, a photoinitiator, a free-radical scavenger, and a thermal initiator. Preferably, the liquid and the powder have the following ingredients with approximate concentration ranges as tabulated:

| Powder | |
|---|---|
| Ingredients | Percentage by Weight |
| Glass | 65-90 |
| Barium tungstate | 0-15 |
| Zinc oxide | 0-10 |
| Na NTG-GMA, NTG-GMA | 2-15 |
| Ethyl 4-dimethylamino benzoate | 0.1-2 |

| Liquid | |
|---|---|
| Ingredients | Percentage by Weight |
| Ethoxylated bisphenol A dimethacrylate | 50-80 |
| 2-Hydroxyethyl methacrylate | 10-25 |
| PMDM | 2.5-17 |
| Polyacrylic acid | 1-5 |
| 2,3-bornanedione | 0.05-0.25 |
| Butylated hydroxytoluene | 0.001-1.0 |
| Benzyl peroxide | 0.005-0.05 |
| d-Tartaric acid | 0.10-1.0 |
| 2,2-hydroxy-5-tert octyl phenylbenztriazole | 0.5-2.5 |

The powder and the liquid are preferably mixed together in a weight ratio of about 2:1 to about 1:1, depending on the particular viscosities of the dental composition that is desired.

Mixing may be done immediately before the dental composition is applied to a patient under normal room lighting conditions. Typically, illumination will vary in intensity from about 80 to about 100 foot candles.

When it is desired to initiate curing, the mixed material is exposed to the output from a dental visible light curing unit. For all examples cited herein, a Visar curing light marketed by Den-Mat, Inc., Santa Maria, Calif., was used. This unit utilizes a type EKE or EJV quartz-halogen light bulb, operating at 21 VAC. The light is transmitted to the work site by a flexible fiber-optic bundle ¼-inch in diameter by four feet in length. The output of the unit used is $180 \times 10^4$ Candela per square meter, giving illumination of about 20,000 foot candles on the material being cured. Satisfactory operability can be achieved with 5,000 foot candles.

Under these conditions, the material cures in about 10 seconds to about 30 seconds. Otherwise, upon standing for about 5 minutes to about 30 minutes under normal lighting conditions, the material cures thermally.

Paste-Paste Systems

One paste form comprises a dental filler, a hydrophilic resin, a polymerizable matrix material, a bonding agent, a radiopaquing agent (optional), a buffering agent (optional), and a photoinitiator.

The other paste form comprises a dental filler, a hydrophilic resin, a photoinitiator, a free-radical scavenger, a thermal initiator, a polymeric carboxylic acid, and a coupling agent.

Preferably, the two paste forms have the following ingredients with approximate concentration ranges as tabulated:

| PASTE A | |
|---|---|
| Ingredients | Percentage by Weight |
| Glass | 5-70 |
| 2-Hydroxyethyl methacrylate | 3-40 |

-continued

PASTE A

| Ingredients | Percentage by Weight |
| --- | --- |
| Ethoxylated bisphenol A dimethacrylate | 15–60 |
| 2,3-Bornanedione | 0.03–0.30 |
| Butylated hydroxytoluene | 0.001–1.0 |
| Benzoyl peroxide | 0.005–0.10 |
| Polyacrylic acid | 1–5 |
| PMDM | 2.5–17 |
| d-Tartaric acid | 0.05–0.5 |
| 2,2-Hydroxy-5-tert-octyl phenylbenztriazole | 0.00–1.9 |

PASTE B

| Ingredients | Percentage by Weight |
| --- | --- |
| Glass | 3–70 |
| 2-Hydroxyethyl methacrylate | 0–45 |
| Ethoxylated bisphenol A dimethacrylate | 20–90 |
| Na NTG-GMA, NTG-GMA | 2–15 |
| Zinc oxide | 0–15 |
| Barium tungstate | 0–15 |
| Ethyl 4-dimethylamino benzoate | 0.5–2.0 |
| Titanium dioxide | 0.0–3.0 |
| 2,2-Hydroxy-5-tert-octyl phenylbenztriazole | 0.00–1.9 |

The two pastes, Paste A and Paste B, are preferably mixed in equal amounts.

In a similar manner to the preparation of the powder-liquid system, mixing may be done immediately before application. When so mixed and exposed to a visible light, the material cures within about 30 seconds.

Advantageously, the powder-liquid system, the paste-paste system, and other suitable systems may be packaged and marketed in an article of manufacture or "kit" for use in dentistry. Such an article of manufacture, for example, comprises cartridges or containers. Conveniently, the article of manufacture according to this invention comprises two cartridges or containers. One cartridge (container) contains a first component, e.g., a powder form or a paste form. The other cartridge (container) contains a second component, e.g., a liquid form or another paste form. The kit may further comprise mixing means such as spatula or pipette. By such means, two components can be admixed thoroughly and the resulting dental cement composition can be applied to a tooth. The kit allows two components to be stored separately from the time of manufacture until the time of utilization, thus providing adequate storage stability of each component.

Although this invention has been described by reference to the dental application of the instant composition, it will be appreciated by those skilled in the art that the use is not limited to the dental cement. Taking advantage of the biocompatibility of a preferred embodiment of the instant composition, those skilled in the art can readily formulate, for example, a bone cement. Furthermore, without departing significantly from a typical dental cement composition, the instant composition can be adapted for use as a household or industrial adhesive.

Accordingly, it is intended to embrace all such alternatives, modifications, and all variations as falling within the spirit and broad scope of the appended claims. The following examples further illustrate some specific embodiments of this invention, but are not to be construed as limiting.

EXAMPLE 1

POWDER-LIQUID SYSTEM

The following ingredients were combined and blended uniformly together to produce a powder formulation.

Powder

| Ingredients | Percentage by Weight |
| --- | --- |
| Alumina fluoride silica glass | 81 |
| Barium tungstate | 8 |
| Zinc oxide | 2 |
| Na NTG-GMA | 8 |
| Ethyl 4-dimethylamino benzoate | 1 |

The following ingredients were combined and blended uniformly together to produce a liquid formulation.

Liquid

| Ingredients | Percentage by Weight |
| --- | --- |
| Ethoxylated bisphenol A dimethacrylate | 72.56 |
| 2-Hydroxyethyl methacrylate | 17.35 |
| PMDM | 5.00 |
| Polyacrylic acid | 2.94 |
| 2,3-bornanedione | 0.15 |
| Butylated hydroxytoluene | 0.02 |
| Benzyl peroxide | 0.03 |
| d-Tartaric acid | 0.15 |
| 2,2-hydroxy-5-tert octyl. phenylbenztriazole | 1.80 |

The powder and the liquid were mixed together in a ratio by weight of about 2:1, powder to liquid, just prior to application. Mixing took about twenty seconds.

Working time was about 1–2 minutes. The curing time was about less than thirty seconds on exposure to a dental curing light.

EXAMPLE 2

PASTE-PASTE SYSTEM

The following ingredients were combined and blended uniformly together to produce a paste formulation.

PASTE A

| Ingredients | Percentage by Weight |
| --- | --- |
| Alumina fluoride silica glass | 56.31 |
| 2-Hydroxyethyl methacrylate | 13.5 |
| Ethoxylated bisphenol A dimethacrylate | 19.5 |
| 2,3-Bornanedione | 0.01 |
| Butylated hydroxytoluene | 0.4 |
| Benzoyl peroxide | 0.04 |
| Polyacrylic acid | 2.37 |
| PMDM | 5 |
| Silica glass | 2 |
| Tartaric acid | 0.12 |
| 2,2-Hydroxy-5-tert-octyl phenylbenztriazole | 0.66 |

PASTE B

| Ingredients | Percentage by Weight |
| --- | --- |
| Alumina fluoride silica glass | 55 |
| Ethoxylated bisphenol A dimethacrylate | 31.4 |
| Na NTG-GMA | 8 |
| Ethyl 4-dimethylamino benzoate | 1 |
| Silica glass | 4 |

-continued
PASTE B

| Ingredients | Percentage by Weight |
| --- | --- |
| 2,2-Hydroxy-5-tert-octyl phenylbenztriazole | 0.6 |

The two pastes are mixed in equal quantities, just prior to application. Mixing time, working time, and curing time are approximately the same as for the powder-liquid system described above.

EXAMPLE 3

The following ingredients were combined and blended uniformly together to produce a paste formulation.

PASTE A

| Ingredients | Percentage by Weight |
| --- | --- |
| Barium alumina fluoride silica glass | 60.60 |
| Silica glass | 2.06 |
| 2-Hydroxyethyl methacrylate | 11.69 |
| Ethoxylated bisphenol A dimethacrylate | 16.90 |
| 2,3-bornanedione | 0.11 |
| Butylated hydroxytoluene | 0.01 |
| Benzoyl peroxide | 0.05 |
| Polyacrylic acid | 2.53 |
| PMDM | 5.34 |
| d-Tartaric acid | 0.13 |
| 2,2-Hydroxy-5-tert-octyl phenylbenztriazole | 0.58 |

PASTE B

| Ingredients | Percentage by Weight |
| --- | --- |
| Barium alumina fluoride silica glass | 58.5 |
| Silica glass | 4.0 |
| Ethoxylated bisphenol A dimethacrylate | 27.5 |
| Na NTG-GMA | 8.5 |
| Ethyl 4-dimethylamino benzoate | 1.0 |
| 2,2-Hydroxy-5-tert-octyl phenylbenztriazole | 0.5 |

The two pastes are mixed in equal quantities, just prior to application. Mixing time, working time, and curing time are approximately the same as for the powder-liquid system described above.

EXAMPLE 4
PASTE-PASTE SYSTEM

The following ingredients were combined and blended uniformly together to produce a paste formulation.

PASTE A

| Ingredients | Percentage by Weight |
| --- | --- |
| Silica glass | 8.19 |
| 2-Hydroxyethyl methacrylate | 33.76 |
| Ethoxylated bisphenol A dimethacrylate | 50.26 |
| 2,3-bornanedione | 0.10 |
| Butylated hydroxytoluene | 0.02 |
| Benzoyl Peroxide | 0.06 |
| Polyacrylic acid | 2.48 |
| PMDM | 5.01 |
| d-Tartaric acid | 0.12 |

PASTE B

| Ingredients | Percentage by Weight |
| --- | --- |
| Silica glass | 7.53 |
| Ethoxylated bisphenol A dimethacrylate | 82.62 |
| Na NTG-GMA | 8.0 |
| Ethyl 4-dimethylamino benzoate | 1.0 |
| Titanium dioxide | 0.85 |

The two pastes are mixed in equal quantities, just prior to application. Mixing time, working time, and curing time are approximately the same as for the powder-liquid system described above.

EXAMPLE 5

A series of tests was performed on the dental material of Example 3 as well as on a commerically-available light-curing composite for a comparison purpose. The results obtained are shown in the following table:

TABLE 1

|  | Material of Invention Example 3 | Commercial Ionomer Cement* |
| --- | --- | --- |
| Form | Powder/Liquid |  |
| pH | Neutral | 3.7 |
| Compressive Strength (24 hrs.) | 16,000 psi | 7,400 psi |
| Diametral Tensile Strength | 6,000 | 1,000 |
| Shear Strength | 1,700 | 160 |

*A glass ionomer cement available from Premier Corp. under the trademark "KETAC."

The above test results indicate that the material produced from the dental composition of the present invention has a physiologically neutral pH, superior strength properties when cured, and provides a source of leachable fluoride ions.

EXAMPLE 7

The composition of Example 3 was tested for its bond strength against various substrates, including those in dentistry. Thus, shear bond testing was conducted according to the following protocol with the results indicated in Table 2.

DENTIN

Bovine teeth are ground to expose the dentin surface with a Foster Model Trimmer using 36 silicon carbide grit. The teeth are then placed in a cold acrylic compound mold. The dentin is treated with a dental conditioner (dichloromethane solution) for one minute and then washed with water and air dried. The test material is placed on the dentin and light cured for about one minute. A dental composition is placed in a 5.3 mm dia gelatin capsule and placed on the cured test material and the capsule is then light cured. The samples are then placed in 37° C. water and stored (normally 24 hours). The sheer bond strength is then determined using an instron 1000 instrument.

ENAMEL

A smooth enamel surface is obtained on the bovine teeth using the Foster Model Trimmer. The same procedure for dentin is then followed for enamel.

PORCELAIN

Circular disks of Cerinate porcelain (Den-Mat Corporation) 20 mm dia×2 mm thick are used for bond strengths. The disks are placed in cold acrylic molds.

The porcelain is normally either etched with hydrofluoric acid for one minute, roughened with a dental burr or sandblasted. The porcelain is treated with the dental conditioner for one minute, rinsed with water and air dried. The same procedure then is followed for the shear bond strength determination.

METAL

The metal surfaces (usually metal bars 8 mm×10 mm×2 mm thick) are also placed in cold acrylic molds. The surfaces are normally roughened with a dental burr or sandblasted.

The surfaces are treated with the dental conditioner for about one minute. The composite capsule is placed on the surface and the shear bond strength is measured.

The metals used in the test have the following basic compositions:
  Gold: Approximately 86% Gold, 4% Pt, 6% Pd
  Non-Precious Metal (Rexillium III): About 75% Ni, 13% Cr, 5% Mo, 1% Be
  Amalgam: Contains silver, mercury with copper dispersion.

TABLE 2

| Substrate | Shear Bond Strength (psi) |
|---|---|
| Dentin | 1731 |
| Enamel | 2000 |
| Porcelain | 3368 |
| Gold | 1702 |
| N/P Metal | 1298 |
| Stainless Steel | 3216 |
| Amalgam | 1017 |

The above results indicate that the composition of the present invention strongly bonds to a variety of substrates.

The invention now being fully described, it will be apparent to one of ordinary skill in the art that many changes and modifications can be made without departing from the spirit or scope of the invention.

We claim:

1. An adhesive composition useful for dental restoration consisting essentially of:
    (a) a finely-divided, from about 0.005 to about 500 microns, reinforcing filler;
    (b) a methacrylate-functional resin;
    (c) a bonding agent selected from the group consisting of (i) N-phenylglycin, the alkali metal salt thereof, or the mixture of the foregoing two compounds, (ii) the adduct of N(P-tolyl) glycine and glycidyl methacrylate, the alkali metal salt thereof, or the mixture of the foregoing two compounds, (iii) the adduct of N-phenylglycine and glycidyl, the adduct of bisphenol A and glycidyl methacrylate, the alkali metal salt thereof, or the mixture of the foregoing two compounds, and N-(p-tolyl) glycine;
    (d) a coupling agent selected from the group consisting of (i) the adduct of pyromellitic acid dianhydride and 2-hydroxyethylmethacrylate, (ii) the adduct of 3,3'4,4'-benzophenonetetracarboxylic dianhydride and 2-hydroxyethyl methacrylate, and (iii) 4-methacryloxyethyltrimellitic; and
    (e) a thermal initiator.

2. The composition according to claim 1, wherein the finely-divided reinforcing filler is selected from the group consisting of porcelain, ceramic fibers, zirconium oxide and borosilicate glass.

3. The composition according to claim 1, wherein the polymerizable matrix material is selected from the group consisting of ethoxylated bisphenol A dimethacrylate, adduct of bisphenol A and glycidyl methacrylate, and the mixture of either of the foregoing two compounds with bisphenol A dimethacrylate.

4. The composition according to claim 1, wherein the bonding agent is sodium adduct of N(P-tolyl) glycine and glycidyl methacrylate.

5. The composition according to claim 1, wherein the coupling agent is an adduct of pyromellitic acid dianhydride and 2-hyroxyethylmethacrylate.

6. The composition according to claim 1, wherein the thermal initiator is benzoyl peroxide.

7. The composition according to claim 1, further comprising a photoinitiator.

8. The composition according to claim 7, wherein the photoinitiator is a photosensitive exciplex donor-acceptor combination of 2,3-bornanedione and ethyl 4-dimethylamino benzoate.

* * * * *